United States Patent [19]

Lang

[11] Patent Number: 4,959,057
[45] Date of Patent: Sep. 25, 1990

[54] CATHETER FOR ORGAN PERFUSION

[75] Inventor: Thomas Lang, Hamburg, Fed. Rep. of Germany

[73] Assignee: Fresenius Ag, Gluckensteinweg, Fed. Rep. of Germany

[21] Appl. No.: 327,941

[22] Filed: Mar. 23, 1989

[30] Foreign Application Priority Data

May 28, 1988 [DE] Fed. Rep. of Germany ... 8807003[U]

[51] Int. Cl.⁵ .......................................... A61M 25/00
[52] U.S. Cl. .................................... 604/264; 604/280
[58] Field of Search ............... 604/264, 280, 178, 175

[56] References Cited

U.S. PATENT DOCUMENTS 3,788,328  1/1974  Alley et al. ..................... 604/178
4,392,855  7/1983  Oreopoulos et al. ............ 604/280

Primary Examiner—Stephen C. Pellegrino
Attorney, Agent, or Firm—Henderson & Sturm

[57] ABSTRACT

Catheter comprising a catheter shank 2 and a lateral opening 9 spaced from the front open end 4 thereof in which spaced from the lateral opening 9 a conical sealing ring 7 with rearwardly increasing diameter is disposed on the outer wall of the catheter shank 2.

5 Claims, 1 Drawing Sheet

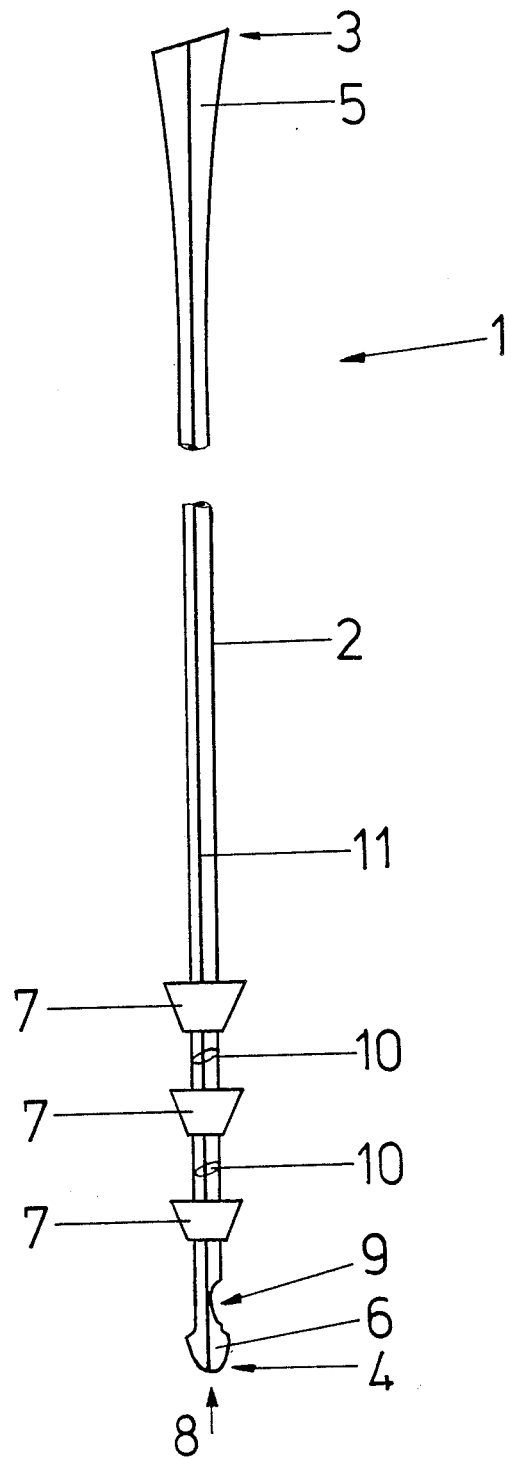

CATHETER FOR ORGAN PERFUSION

The invention relates to a catheter for organ perfusion comprising a catheter shank which has a lateral opening spaced from the distal end thereof and an atraumatic widening and at the proximal end connecting means for medical apparatuses.

Perfusion serves to conserve human donor organs, the organs being flushed through with the perfusate. For this purpose the perfusion system comprises a suitable perfusion catheter which is introduced into an organ of the human body. This catheter consists of a flexible tube which is made from plastic and the connection piece of which becomes larger in funnel manner at the proximal end and thus permits an adaptation to the perfusion system so that a smooth connection without cross-sectional change takes place. To this funnel-like enlargement medical devices such as syringes, cannulas, tubings or the like may be connected which also have a funnel-like or conical connecting piece. As a rule, the perfusion catheters have an atraumatically shaped point at their distal end to prevent possible vascular damage on introduction of the catheter into the organ or the organ vessel. After snaring of the catheter and incision of the organ vessel the catheter is introduced into the organ vessel. After placement of the catheter the latter is fixed by means of ligature. This fixation had however the disadvantage that the incision point was not adequately sealed and as a result the perfusate emerged from the incision point. Moreover, the perfusion catheter was not adequately arrested at the incision point.

The problem of the invention is now to further develop a catheter for organ perfusion in such a manner that it seals the incision point of the organ to be perfused, fixes itself in position and ensures adequate drainage.

According to the invention the problem is solved in that the catheter shank comprises at its outer wall spaced from its lateral opening at least one sealing ring widening conically in the direction of the proximal end. The catheter shank may however also comprise a plurality of spaced-apart sealing rings. The latter can either be an integral part of the catheter shank or parts subsequently applied to the catheter shank.

The catheter, which consists of medically compatible plastic, for example polyurethane, is introduced through the incision point into the organ vessel, the sealing ring or rings penetrating with their tapered end first into the organ. On further advancing of the catheter the incision point is gradually widened by the conical form of the sealing rings until the vessel contracts behind the wide end of the conical sealing ring and engages round the catheter shank. In addition, the catheter may be fixed distally of the sealing ring by means of ligature. Due to the conical sealing ring a complete sealing of the incision point and arresting of the perfusion catheter in the organ vessel is achieved.

To facilitate the introduction of the perfusion catheter the conical sealing rings may consist of a softer plastic material than the catheter shank so that the sealing ring on introduction of the catheter shank can contract on passing the incision point and the incision point is thus not unnecessarily widened or stretched.

In a particular embodiment of the invention the conical sealing rings may consist of the same material as the catheter tube and be integral therewith. This has considerable production technical advantages. In another embodiment the sealing rings may be subsequently applied to the catheter shank, for example by shrinking on.

The lateral opening adjacent the opening tip gives a large lumen to ensure adequate discharge so that the organs to be perfused can be perfused in a short time with the solutions used for this purpose, for example Eurocollins solutions. Preferably, the distance of the lateral opening in the catheter shank with an outer diameter of 6–10 mm from the open tip angled at an angle of 30°–60° is 3–6 mm and the lateral opening is 6–8 mm long in the longitudinal direction of the catheter shank and 3–5 mm wide in the peripheral direction. Particularly preferred is a tip of the catheter angled at 45° in which the front end of the lateral opening aligns with the bevelled end of the catheter tip and the lateral opening has a distance from the outermost catheter tip corresponding to the length of the bevel. The opening is 7 mm long and 4 mm wide for an outer diameter of the catheter of 6 or 8 mm.

The distance of the front end of the sealing ring secured to the outer surface of the catheter shank from the rear end of the lateral opening is 7–10 mm, the sealing ring having a length of 5–12 mm. Preferably, the distal distance from the catheter tip is about 15 mm.

The outer diameter of the sealing ring at the free rear end may be 8–12 mm, preferably 9.9–11.3 mm.

The catheter may have a length of 30 cm to 1 m and the catheter shank is widened in diameter slightly in funnel-like manner at the rear end for connection to corresponding appliances so that pushing onto a tube connecting piece is possible or is provided with a so called Luer connector which is so dimensioned that the cross-sectional constriction in the region of the Luer connection compared with the inner diameter of the catheter is a minimum. This ensures an adequate seal so that organs can be perfused in a very short time with the catheter according to the invention. The drawing FIGURE shows a perspective view of the perfusion catheter of this invention.

The drawing FIGURE shows a perspective view of the perfusion catheter of this invention.

The invention will now be explained in detail with reference to an example of embodiment.

The attached drawing shows a perfusion catheter 1 which consists of a catheter shank 2. The latter comprises a proximal end 3 and a distal end 4. The proximal end 3 is made funnel-shaped and serves as connection means 5 for medical appliances or apparatuses such as syringes, cannulas, tubings, etc., which have a conical connection. The cone thereof is inserted into the funnel-shaped connection means 5 and clamped by the elastic property of the catheter shank 2 consisting of silicone material so that a smooth connection without cross-sectional change takes place from the perfusion system to the perfusion catheter 1. Via this funnel-shaped connector 5 the perfusate is subsequently introduced into the catheter shank 2 and further on into the organ vessel to rinse through the latter.

The distal end 4 of the catheter shank 2 comprises an atraumatically shaped tip 6 which preferably has the form of an abacus bead. This prevents vascular damage on introduction of the perfusion catheter 1.

In the region of the distal end 4 of the catheter shank 2 one or more sealing rings 7 widening conically in the direction of the proximal end 3 are arranged spaced apart from each other. Said rings can be an integrated part of the catheter shank 2 or consist of the same material as the catheter shank 2. On the other hand, said sealing rings 7 may consist of another preferably softer material and be subsequently applied to the catheter shank 2, for example by shrinking on.

The distal end 4 of the catheter shank 2 has the main outlet lumen 8. In the immediate vicinity of said main outlet lumen 8 an additional lateral opening 9 is disposed which ensures a perfusion should the main outlet lumen 8 bear on the vascular intima.

In a further embodiment of the invention, in particular when several conical sealing rings 7 are arranged spaced apart on the catheter shank, special premarked separating points 10 may be disposed between said sealing rings and formed as desired breakage points. This enables the perfusion catheter 1 to be adapted to the specific organ and the introduction depth defined in that the catheter shank 2 is severed at a specific separating point 10 so that the catheter 1 is shortened and accordingly adapted to the specific organ. In addition, the perfusion catheter may be formed in different diameters for respective different organs. Furthermore, the catheter shank 2 may be provided with an X-ray strip 11. The perfusion catheter 1 is introduced with its atraumatically formed tip 6 disposed at the distal end first through the incision point into the organ vessel. The sealing ring 7 passes the incision point and widens the latter by its conical form until the incision point has passed the largest diameter of the conical sealing ring 7 and engages behind the latter round the catheter shank 2. As a result the incision point of the organ vessel is completely and reliably sealed and the perfusion catheter 1 fixedly located in the organ.

I claim:

1. A catheter for vessel perfusion including an elongated tubular shank having proximal and distal ends, characterized in that the distal end is atraumatically enlarged in the form of a bead, a first sealing ring concentric with the shank is fixedly carried by the shank and closely spaced in the proximal direction from the distal end, a second sealing ring concentric with the shank is fixedly carried by the shank and closely spaced in the proximal direction from the first ring, and each sealing ring is of conical form widening in the proximal direction, and a lateral opening is provided in the wall of the shank intermediate the distal end and the first ring.

2. Catheter according to claim 1, characterized in that the sealing rings are an integrated part of the catheter shank.

3. Catheter according to claim 1, characterized in that the sealing rings are parts subsequently applied to the catheter shank.

4. Catheter according to claim 1, characterized in that the sealing rings consist of the same material as the catheter shank.

5. Catheter according to claim 1, characterized in that the sealing rings consist of a plastic which is softer than the material of the catheter shank.

* * * * *